(12) United States Patent
Delile et al.

(10) Patent No.: US 11,629,369 B2
(45) Date of Patent: Apr. 18, 2023

(54) ELECTROCHEMICAL STRIPS FOR MONITORING THE DEGRADATION OF BODY FAT AND METHOD FOR PREPARING SAME

(71) Applicant: LSEE, Ajaccio (FR)

(72) Inventors: Sébastien Delile, Paris (FR); Cyril Torre, Paris (FR)

(73) Assignee: LSEE, Ajaccio (FR)

( * ) Notice: Subject to any disclaimer, the term of this patent is extended or adjusted under 35 U.S.C. 154(b) by 320 days.

(21) Appl. No.: 16/632,295

(22) PCT Filed: Jul. 13, 2018

(86) PCT No.: PCT/FR2018/051781
§ 371 (c)(1),
(2) Date: Jan. 17, 2020

(87) PCT Pub. No.: WO2019/016451
PCT Pub. Date: Jan. 24, 2019

(65) Prior Publication Data
US 2021/0071224 A1    Mar. 11, 2021

(30) Foreign Application Priority Data
Jul. 20, 2017   (FR) ..................................... 1756898

(51) Int. Cl.
| | | |
|---|---|---|
| C12Q 1/00 | (2006.01) | |
| C12Q 1/26 | (2006.01) | |
| C12Q 1/32 | (2006.01) | |
| C12Q 1/48 | (2006.01) | |
| G01N 27/327 | (2006.01) | |

(52) U.S. Cl.
CPC .............. *C12Q 1/005* (2013.01); *C12Q 1/26* (2013.01); *C12Q 1/32* (2013.01); *C12Q 1/485* (2013.01);
(Continued)

(58) Field of Classification Search
None
See application file for complete search history.

(56) References Cited

U.S. PATENT DOCUMENTS

| | | |
|---|---|---|
| 9,103,842 B2 | 8/2015 | Gray et al. |
| 2004/0043376 A1 | 3/2004 | Gupta |

(Continued)

FOREIGN PATENT DOCUMENTS

| | | |
|---|---|---|
| EP | 1873516 B1 | 10/2009 |
| EP | 2812444 B1 | 12/2014 |

(Continued)

OTHER PUBLICATIONS

Ebadi el al., Potential Biomarkers of Fat Loss as a Feature of Cancer Cachexia, Review Article Mediators of Inflammation, vol. 2015, Article ID 820934, (2015), 8 pages.

(Continued)

*Primary Examiner* — J. Christopher Ball
(74) *Attorney, Agent, or Firm* — TraskBritt (57) ABSTRACT

Devices, systems, and methods are used for personalized monitoring of changes in metabolism as a function of external parameters such as food or physical exercise. More particularly, the present disclosure relates to electrochemical strips for detecting the amount of biomarker for fat metabolism, in particular, glycerol.

12 Claims, 4 Drawing Sheets

(52) U.S. Cl.
CPC ..... *G01N 27/3272* (2013.01); *G01N 27/3275* (2013.01); *G01N 2800/7085* (2013.01)

(56) References Cited

U.S. PATENT DOCUMENTS

| | | | | |
|---|---|---|---|---|
| 2005/0164329 | A1* | 7/2005 | Wallace-Davis | C12Q 1/001 435/26 |
| 2005/0178674 | A1 | 8/2005 | Hyland et al. | |
| 2008/0038765 | A1* | 2/2008 | Imamura | C12Q 1/44 435/15 |
| 2010/0015692 | A1* | 1/2010 | Feldman | C12Q 1/001 435/288.7 |
| 2010/0270175 | A1* | 10/2010 | Pei | C12Q 1/006 204/403.14 |
| 2016/0178823 | A1 | 6/2016 | Gupta | |

FOREIGN PATENT DOCUMENTS

| | | |
|---|---|---|
| WO | 88/05912 A1 | 8/1988 |
| WO | 2000/042422 A1 | 7/2000 |
| WO | 2016/097615 A1 | 6/2016 |
| WO | 2016/178823 A1 | 11/2016 |

OTHER PUBLICATIONS

International Search Report for International Application No. PCT/FR2018/051781 dated Dec. 3, 2018, 3 pages.
International Written Opinion for International Application No. PCT/FR2018/051781 dated Dec. 3, 2018, 6 pages.
D. Compagnone et al: "Development of a biosensor for monitoring of glycerol during alcoholic fermentation", Biosens Bioelectron, (Oct. 1998); vol. 13(7-8):875-880.
Degrelle, "DietSee: An on-hand, portable, strip-type biosensor for lipolysis monitoring via real-time amperometric determination of glycerol in blood", Elsevier, Analytica Chimica Acta, 1155 (2021) 338358, 8 pages.
European Communication pursuant to Article 94(3) EPC for European Application No. 18758921, dated Jul. 22, 2022, 5 pages.
Katrlik J et al: "Amperometric biosensors based on two different enzyme systems and their use for glycerol determination in samples from biotechnological fermentation process", Analytica Chimica Acta, vol. 566, Issue 1, (Apr. 27, 2006), pp. 11-18.

* cited by examiner

ELECTROCHEMICAL STRIPS FOR MONITORING THE DEGRADATION OF BODY FAT AND METHOD FOR PREPARING SAME

CROSS-REFERENCE TO RELATED APPLICATIONS

This application is a national phase entry under 35 U.S.C. § 371 of International Patent Application PCT/FR2018/051781, filed Jul. 13, 2018, designating the United States of America and published as International Patent Publication WO 2019/016451 A1 on Jan. 24, 2019, which claims the benefit under Article 8 of the Patent Cooperation Treaty to French Patent Application Serial No. 1756898, filed Jul. 20, 2017.

TECHNICAL FIELD

The present disclosure relates to the field of personalized monitoring of changes in metabolism as a function of external parameters such as diet or physical exercise. The present disclosure relates more particularly to electrochemical strips for detecting the quantity of biomarkers of fat metabolism, in particular, glycerol.

BACKGROUND

An individual's body fat mass evolves according to different parameters, in particular, according to his or her diet and physical activity. The impact of these two parameters on fat mass is now well established. It therefore seems interesting for an individual seeking to lose fat mass to be able to assess the impact of these parameters. A better knowledge of one's metabolism will allow an individual to identify the best combination of diet and exercise for weight loss.

In order to know the direct influence of external parameters on the amount of body fat, it is possible to follow the evolution of biomarkers that reflect fat degradation. Various biomarkers have been described as being associated with lipolysis, such as ketones, free fatty acids and glycerol.

Glycerol is a marker of interest since its quantity in the blood directly reflects lipolysis. Thus, by analyzing the quantity of circulating glycerol, it can be known, at any time, whether the body is drawing on its fat reserves or not, and assess the level of lipolysis. Monitoring the amount of glycerol circulating provides real-time information on the body's degradation of fat. Thus, measuring the lipolysis level of an individual wishing to lose weight provides information on the effectiveness of his dietary and/or physical efforts. Analysis of the amount of circulating glycerol also makes it possible to detect cachexia (non-reversible weight loss) at an early stage and to monitor its evolution in the event of treatment, particularly in individuals with cancer; indeed, in these patients, high lipolysis is a marker of cachexia (Ebadi and Mazurak, 2015, Mediators of inflammation).

It would therefore be particularly interesting to have an easy to use, reliable and accessible means of monitoring the evolution of fat mass.

BRIEF SUMMARY

A system for the detection and quantification of ketones in blood is described in application WO2016/178823. This document describes electrochemical test strips to monitor circulating ketone levels through the presence of hydroxybutyrate dehydrogenase and NAD. These strips have the particularity of allowing the simultaneous quantification of ketones and glucose and are suitable for monitoring blood glucose disorders in diabetic patients.

Strips for measuring fat loss during dieting are described in application US2004/0043376. These strips allow monitoring of circulating ketones in a plasma sample by colorimetry. However, this system is not suitable for whole blood testing. The need to obtain plasma involves processing the sample in the laboratory. On the other hand, electrochemical test strips are commercially available to quantify ketones and therefore to monitor ketosis.

Whole blood glucose detection systems are available to monitor blood glucose levels in people with diabetes. These systems are based on the use of electrochemical test strips and analysis of the amount of glucose present in the blood by amperometry. Such strips are well known and are described, for example, in patent applications EP2812444 and WO200042422.

While the amount of ketones is considered indicative of fat loss, it is not a reliable marker. There is therefore a need for a system to monitor fat degradation based on a marker that is closely correlated with lipolysis.

The present disclosure provides electrochemical test strips for the quantification of glycerol in blood.

Circulating glycerol is a direct result of lipid degradation and reflects the metabolism of body fat mass degradation. It is therefore a particularly relevant biomarker for monitoring fat degradation.

The test strips according to the present disclosure enable an individual to make his or her own test without scientific equipment, using a portable device. The analysis is carried out without any particular knowledge since the result is obtained by simple reading.

Thanks to the present disclosure, a correlation between the food consumed (the diet followed) and its consequences on the fat metabolism can be established in a simple and personalized manner. Similarly, a correlation can be obtained with sports activities, for example, according to their intensity and/or duration. Thus, the present disclosure provides a simple and innovative way to identify the best combination of diet and physical activity to lose weight and achieve one's goals. The device can be connected to an application available on a smartphone or other information technology (IT) support to facilitate data recording, analysis and monitoring over time. The present disclosure also makes it possible to monitor fat degradation in the context of monitoring cachexia associated with a disease, particularly in cancer patients.

Thanks to the electrochemical strips associated with a reading device such as the one described in patent application WO2016/097615, an individual can obtain real-time information on the amount of fat burned. This analysis can be done immediately after physical exertion or a few hours after the initiation of a diet.

DETAILED DESCRIPTION

A first embodiment of the present disclosure comprises an electrochemical test strip for the detection of glycerol in a sample of body fluid comprising:
- an electrically insulating substrate layer
- at least two electrodes so as to have a working electrode, a reference electrode and a counter electrode, the functions of the reference electrode and the counter electrode being performed by one and the same electrode in the configuration of a two-electrode strip
- at least as many electrical tracks as the number of electrodes
- an enzyme layer containing glycerol-specific enzymes selected from (i) glycerol kinase and glycerol phosphate oxidase, or (ii) glycerol dehydrogenase, the enzyme layer being disposed on the electrodes
- a layer of co-factors selected from (i) either adenosine triphosphate (ATP) and magnesium chloride ($MgCl_2$) when the enzymes are glycerol kinase and glycerol phosphate oxidase, (ii) or nicotinamide adenine dinucleotide (NAD+) when the enzyme is glycerol dehydrogenase.
- at least one membrane layer
- a spacer layer located between the electrodes and the top layer, the spacer layer creating a space defining the volume of the measuring chamber
- a measuring chamber for receiving the sample, the chamber at least partially covering the electrodes and the enzyme layer
- a top layer.

The principle of use of this strip is as follows: a sample of biological fluid is deposited in the measuring chamber either directly in the space between the substrate layer and the top layer or via the notch on the top layer when present. Contact of the sample with the working electrode causes an electrochemical reaction thanks to the enzymes present in situ.

In order to use it, the test strip is first inserted into a specific reader equipped with an ammeter; the latter is connected to an application available, for example, on a mobile phone such as a smartphone, capable of interpreting the signals corresponding to the microcurrents generated by the electrochemical reaction. The application then provides a result to the user.

A biological fluid sample can be any sample that may contain glycerol, including a sample of saliva, sweat, tears, blood, etc. In a preferred mode of processing, the biological fluid sample is a blood sample. The volume of a drop of blood to be applied to the test strip is usually between 0.3 and 5 microliters.

The substrate layer provides a supporting function. The material of the substrate layer can be chosen from electrical insulating materials. It can be a plastic material such as polyvinyl chloride, polycarbonate, polysulfone, polyester, polyimide, polyethylene, polypropylene, polyethylene terephthalate, etc., but also other materials such as metals, ceramics, and composite materials. When the substrate layer is not made of an insulating material, it is covered with an insulating layer. Such a substrate layer can be made of passivated aluminum. Thus, "electrically insulating substrate layer" means, in the sense of the present disclosure, either a substrate layer made of an electrically insulating material or, when the substrate layer is not made of an insulating material, a substrate layer covered with an electrically insulating film.

The shape of the substrate can be varied, e.g., rectangular, triangular, complex shape with a notch or rounded end.

Classically, an electrochemical strip has three electrodes, each playing a defined role. The first electrode, known as the "working electrode", is used to measure the product of the enzymatic reaction, whether the product is oxidized or reduced. The second electrode, the so-called "reference electrode", is used to set the reference potential (the potential difference used for the measurement is made between this electrode and the working electrode). The third electrode, called the "counter electrode", is used to compensate for the charges exchanged between the electrolyte solution (i.e., the sample) and the working electrode. The current measured during the measurement is measured between the working electrode and this counter electrode.

Additional electrodes can be added to support other features such as detecting the insertion of the test strip into the meter, detecting the filling of the measuring chamber.

A strip according to the present disclosure comprises at least 2 electrodes, but may also contain 3, 4, 5 or more electrodes, depending on the configuration of the strip and the functions it performs. If the test strip has only two electrodes, the functions of the reference electrode and the counter electrode are performed by one and the same electrode. If the test strip has 3 electrodes, these preferably correspond to the working electrode, reference electrode and counter electrode.

The shape of the electrodes is not binding; for example, they can be rectangular and have a contact surface with the biological fluid sample of between 0.5 and 2 $mm^2$.

The working electrode is preferably made of carbon or platinum, but can also be made of other metals, metal alloys or conductive polymers.

In a particular embodiment, the working electrode is made of platinum. Preferably, such an electrode is not functionalized.

In another special embodiment, the working electrode is made of carbon and is functionalized by the addition of Prussian blue. Other catalysts may alternatively be applied to the working electrode such as ferri/ferrocyanide ions, osmium complexes, ferrocene or one of its derivatives such as ferrocene-methanol, a redox polymer (of the polyaniline, polypyrrole, poly-ferrocene type), tetramethylbenzidine.

In a preferred embodiment, the electrode is made of carbon and is functionalized by the addition of ferrocene methanol.

The reference electrode preferably contains silver or silver chloride, but can also be made with other metal oxides or salts, in particular, silver, or with a redox polymer, in particular, a poly-ferrocene.

The counter electrode may be made of any suitable conductive material such as carbon, platinum, silver or any other metal or other conductive material.

The strip has a number of electrical tracks at least equal to the number of electrodes, i.e., at least two. The test strip may have tracks not connected to electrodes; for example, a track not connected to an electrode may be used to allow the meter to detect the test strip. Electrical tracks are preferably made of carbon but can also be made of metal such as silver or copper. Their width may be between 0.1 and 1 mm, and their length must be sufficient to connect the connectors to the electrodes.

The enzyme layer on the strip must be specific for the biomarker to be detected, i.e., glycerol. Once in contact with glycerol, the enzyme (or enzymes) modifies it (them), thanks to its (their) catalytic properties. This modification can reveal the presence of modified glycerol or glycerol co-products by detecting microcurrents at the electrodes, but also quantifies the glycerol present in the sample. The enzyme layer is applied at least to the working electrode, but can also be applied over the entire electrode surface.

In a first mode of implementation, the enzymes chosen to reveal the presence of glycerol are glycerol kinase and glycerol phosphate oxidase. Optionally, the strip may also contain peroxidase.

In a special embodiment, the enzyme layer containing glycerol kinase and glycerol phosphate oxidase also contains peroxidase. In another special embodiment, peroxidase can be contained in a separate layer.

In a second mode of implementation, the enzyme chosen to reveal the presence of glycerol is glycerol dehydrogenase. Optionally, the strip also contains diaphorase.

In a special embodiment, the enzyme layer containing glycerol deshydrogenase also contains diaphorase. In another special embodiment, diaphorase can be contained in a separate layer.

The strip also contains co-factors that work with the specific glycerol enzyme chosen.

When the enzymes are glycerol kinase and glycerol phosphate oxidase, the co-factors are adenosine triphosphate (ATP) and magnesium chloride ($MgCl_2$). When the enzyme is glycerol dehydrogenase, the co-factor is nicotinamide adenine dinucleotide (NAD+).

The stacking of the layer of enzyme(s) and co-factor(s) on the working electrode constitutes the "sensitive layer". This sensitive layer allows the detection of glycerol. It is necessarily located between the substrate layer and the top layer but its internal arrangement may vary. In particular, the order of the enzyme(s) and co-factor(s) layers may vary. On the other hand, the layers of enzyme(s) and co-factor(s) may be distinct or included in the same layer as mentioned above. The sensitive layer can be applied only to the working electrode or can be the same size as the measuring chamber without affecting the function of the test strip.

The sensitive layer does not include the working electrode. However, when it is functionalized, the working electrode participates in the reaction and can therefore be considered as belonging to the sensitive layer.

The sensitive layer according to the present disclosure also contains a membrane layer. This membrane layer can have different functions such as keeping the other constituents close to the electrode, blocking interferents (filtering), enriching the layer with oxygen, etc., and several membrane layers can be added in the same sensitive layer. Such a layer can be made of different materials depending on the desired function. A layer of chitosan membrane is preferentially added, especially to maintain the surface enzymes, but a layer of NAFION®, hydroxymethyl cellulose, hydroxypropyl methyl cellulose, cellulose acetate, poly (4-vinylpyridine) membrane, etc., can also be chosen.

In a preferred embodiment, the sensitive layer comprises, in addition to enzymes and co-factors, a chitosan membrane containing glutaraldehyde.

In another preferred embodiment, the sensitive layer comprises, in addition to enzymes and co-factors, a hydroxypropyl methyl cellulose membrane.

In a particular embodiment, the sensitive layer may contain a surfactant. This can be added at different levels. Surfactants can be used to modify the surface voltage properties of the electrode or substrate, to guide the sample over the electrode or more generally to improve deposition processes. They can also be used to improve the solubility of constituents during deposition. As an example, such surfactants can be selected from sodium dodecyl sulphate (SDS), Triton X-100, etc.

In a preferred embodiment, the sensitive layer contains a surfactant. A particularly preferred surfactant is Triton X-100.

In a highly preferred embodiment, the sensitive layer comprises enzymes glycerol kinase, glycerol phosphate oxidase and peroxidase, co-factors ATP and $MgCl_2$, hydroxypropyl methyl cellulose, ferrocene methanol and a surfactant. This sensitive layer can be deposited in a single layer containing all the components of the sensitive layer.

In another particular embodiment, the sensitive layer may contain cross-linking agents (allowing cross-linking). These are preferentially added to the membrane layer at the time of deposition. They may also be applied with or between the enzyme or co-factor layers, as well as between the enzyme and co-factor layers or between the enzyme layer or membrane depending on the desired effect. A preferred cross-linking agent is glutaraldehyde, but others such as PEDGE (polyethylene glycol diglycidyl ether), EDC/NHS (hydrochlorinated 1-ethyl-3-(3-dimethylaminopropyl)carbodiimide/N-hydroxysuccinimide), or others may be used.

The sensitive layer may therefore contain, in addition to enzymes, co-factors, and the membrane layer, and a surfactant, at least one cross-linking agent.

In a special embodiment, the sensitive layer comprises Prussian blue, the enzymes glycerol kinase and glycerol phosphate oxidase, the co-factors ATP and MgCl2, a chitosan membrane layer and glutaraldehyde as cross-linking agent.

In another special embodiment, the sensitive layer does not contain Prussian blue, but contains the enzymes glycerol kinase and glycerol phosphate oxidase, the co-factors ATP and MgCl2 and a membrane layer of hydroxypropyl methyl cellulose. It may also contain peroxidase, ferrocene methanol and a surfactant.

Figure 1:
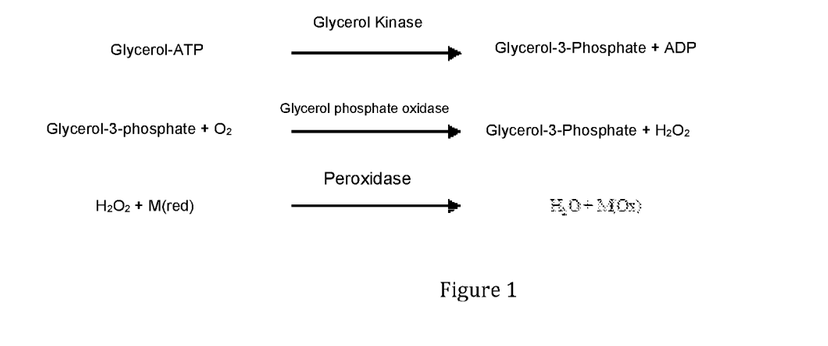
FIG. 1 is a schematic representation of enzymatic reactions for the quantification of glycerol involving glycerol kinase and glycerol phosphate oxidase, and optionally peroxidase.
Figure 2:
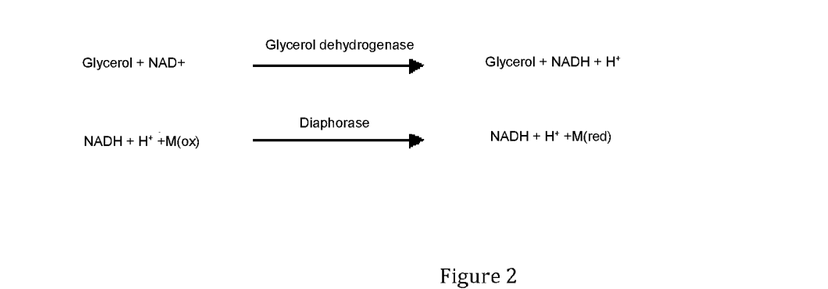
FIG. 2 is a schematic representation of enzymatic reactions for the quantification of glycerol involving glycerol dehydrogenase, and optionally diaphorase.
Figure 3:
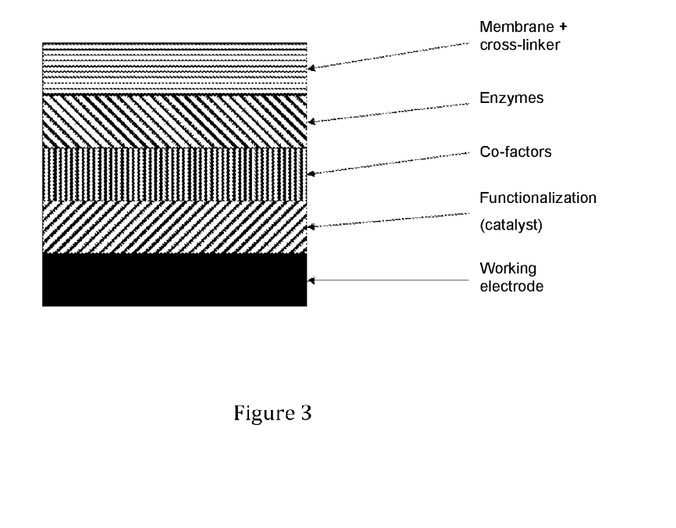
FIG. 3 is a representation of a stack of a sensitive layer positioned in a measuring chamber and suitable for quantifying lipolysis.

FIG. 3 shows an example of the stacking of the different layers constituting a sensitive layer, in other words a functional arrangement of the layers allowing the detection of the presence of glycerol in the measuring chamber.

A spacer layer applied between the electrodes and the top layer, the spacer layer creating a space defining the volume of the measuring chamber. In addition, this spacer layer insulates the electrodes.

In a particular embodiment, the electrode surface, which is exposed to the sample can be delimited by an additional thin insulating layer arranged between the electrodes and the spacer layer.

This spacer layer may consist of an electrically insulating material such as plastic or ceramic or of a non-insulating material covered with a thin insulating layer. Its shape will be generally identical to that of the substrate layer minus the portion corresponding to the measuring chamber. In a special embodiment, a channel can be created between the edge of the test strip and the measuring chamber to allow the sample to be moved by capillary action toward the measuring chamber.

Finally, a top layer covers the strip. It delimits the upper part of the measuring chamber and protects all layers of the test strip. It may have an opening or notch to facilitate the deposit of the sample. It may also contain a vent. It can be made in any suitable material such as a polymer and will preferably have a thickness of the order of a few tens of µm.

Figure 4:
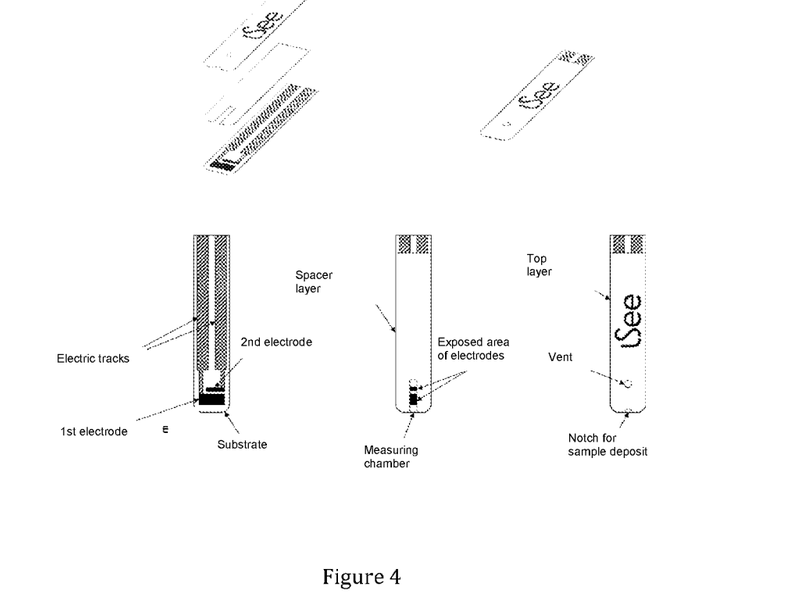
FIG. 4 is a representation of an electrochemical test strip for the detection of glycerol.

FIG. 4 shows an exemplary diagrammatic view of a strip according to the present disclosure.

As an indication, the size of an electrochemical strip is usually of the order of 0.5 to 1 cm wide, 3 to 5 cm long, and 0.05 to 0.5 mm thick. It must be rigid enough to be inserted into the reader.

A second embodiment of the present disclosure relates to a process for preparing an electrochemical strip according to the present disclosure comprising the steps of depositing the following elements:

- an electrically insulating substrate layer
- at least two electrodes
- at least as many electrical tracks as the number of electrodes
- an enzyme layer containing glycerol-specific enzymes, either glycerol kinase and glycerol phosphate oxidase, or glycerol dehydrogenase, the enzyme layer being deposited on the electrodes, or
- a layer containing co-factors selected from adenosine triphosphate (ATP) and MgCl2 when the enzymes are glycerol kinase and glycerol phosphate oxidase,
- nicotinamide adenine dinucleotide (NAD+) when the enzyme is glycerol dehydrogenase
- at least one membrane layer
- a spacer layer located between the electrodes and the top layer,
- a top layer, the top layer being pierceable by a notch to facilitate the deposition of the sample.

In a preferred embodiment, the electric tracks are deposited by screen printing. They can also be deposited by engraving, photolithography or any other technique known to the person skilled in the art.

In a special embodiment, the enzyme, co-factor and membrane layers are deposited (dropcasting) and then dried, but they can also be applied by inkjet printing, spraying, dip-shrinking, etc. Enzymes and co-factors can be deposited in two separate layers or simultaneously in a single layer. In a preferred strip embodiment, the enzymes, co-factors and membrane are contained in a single layer. When the carbon electrode is functionalized by adding ferrocene methanol, the ferrocene methanol can be added directly to the working electrode prior to deposition of the sensitive layer. However, in a preferred embodiment, when all the components of the sensitive layer are deposited simultaneously in a single layer, it may be added at the same time by adding to the solution of the sensitive layer. Thus, all the components to be deposited on the electrode are deposited in a single layer.

The process for preparing the strips according to the present disclosure may also include the deposition of a layer of an additional enzyme. These additional enzymes can be deposited in a single layer with the glycerol-specific enzyme or in a separate layer. Where the sensitive layer comprises an additional enzyme, the (total) enzymes may be deposited together, one after the other or by depositing the co-factor layer between the (base) and additional enzymes. In a preferred embodiment, the additional enzyme is first deposited directly onto the electrode. However, when the sensitive layer is deposited at one time and includes all components, the additional enzyme is added at the same time as the other components.

When the specific enzymes in glycerol are glycerol kinase and glycerol phosphate oxidase, the additional enzyme is peroxidase.

When the specific enzyme in glycerol is glycerol dehydrogenase, the additional enzyme is diaphorase.

When the working electrode is made of carbon, it can be functionalized by adding a solution chosen, for example, from Prussian blue, ferri/ferrocyanide ions, osmium complexes, ferrocene or one of its derivatives such as ferrocenemethanol, a redox polymer (of the polyaniline, polypyrrole, poly-ferrocene type), tetramethylbenzidine. For example, when the electrode is functionalized by adding a Prussian blue solution, this solution is then deposited and then activated at a high temperature, for example, between 80° C. and 100° C., then rinsed with a solution such as water, an organic solvent or a buffer solution, and then dried. When the electrode is functionalized by adding a solution of ferrocene or one of its derivatives, this solution is deposited and then dried at 40° C. for 5 min. Other techniques known to the person skilled in the art can also be used, including no-rinse techniques, or other techniques such as inkjet, spray, electro-deposit printing, etc.

When cross-linking agents are added to the strip layers, they are preferentially added to the membrane layer at the time of deposition. However, cross-linking agents may also be applied with or between the enzyme or co-factor layer. When enzymes, co-factors and membrane are added in a single layer, the cross-linking agents can be deposited simultaneously.

The deposition of an enzyme layer, a co-factor layer and a membrane layer constitutes the sensitive layer of the strip. In particular ways of carrying out the present disclosure, additional layers may be added to the sensitive layer, such as an additional enzyme layer, at least one crosslinker and at least one surfactant. The arrangement of these layers with each other and the possibility of simultaneous deposition of several components in one layer have been described above and apply to the present preparation process.

In a preferred embodiment of the process for preparing the strips according to the present disclosure, the deposition of the elements of the sensitive layer is carried out in a single step. Thus, the following can be added simultaneously:

- the enzymes glycerol kinase and glycerol phosphate oxidase, the co-factors ATP and MgCl2 and an hydroxypropyl methyl cellulose membrane layer;
- the enzymes glycerol kinase and glycerol phosphate oxidase, the co-factors ATP and MgCl2 and an hydroxypropyl methyl cellulose membrane layer;
- the enzymes glycerol kinase, glycerol phosphate oxidase and peroxidase, the co-factors ATP and MgCl2, an hydroxypropyl methyl cellulose membrane;

the enzymes glycerol kinase, glycerol phosphate oxidase and peroxidase, the co-factors ATP and MgCl2, an hydroxypropyl methyl cellulose membrane, ferrocenemethanol.

A third embodiment of the present disclosure relates to the use of an electrochemical test strip according to the present disclosure for assessing lipolysis in an individual from a sample of biological fluid.

Indeed, the electrochemical strips according to the present disclosure contain enzymes for detecting and quantifying glycerol present in a blood sample.

A fourth embodiment of the present disclosure concerns a method for evaluating fat degradation in an individual consisting of:
- inserting the strip into a meter with an ammeter
- sampling a drop of blood
- depositing the drop of blood on an electrochemical strip according to the present disclosure
- waiting for the ammeter reader to perform the electrochemical measurement
- reading the displayed result either directly from the meter or remotely from a device connected to the meter.

This method of assessing fat degradation may also include a step for optimizing fat loss in an individual by correlating the measured fat degradation with the nutrients ingested and/or the type of physical exercise practiced. Thus, the user can deduce the impact of the food ingested and/or the physical exercise practiced on the degradation of the fat mass and this allows him to adapt his behavior according to the results obtained. This type of information can also be processed using an adapted application that will guide the user toward the dietary behaviors and/or the type of physical exercise that is most beneficial to obtain fat degradation.

This method of evaluation also makes it possible to monitor cachexia, especially in patients with cancer.

A meter suitable for this type of method is an apparatus comprising an ammeter, capable of recovering the electrochemical signal emitted by the strip and transmitting it for interpretation either to an internal system or meter or to a remotely connected device.

An example of a reader suitable for such use and a method for monitoring changes in body fat mass are described in patent application WO2016/097615.

For the realization of the strips according to the present disclosure, the various embodiments can be combined with each other, in particular, the preferred embodiments.

The present disclosure shall be better understood by reading the following examples, which are provided by way of illustration and shall in no way be regarded as limiting the scope of the present disclosure.

EXAMPLES

Example 1: Preparation of an Electrochemical Test Strip for the Detection of Glycerol a. Strip produced by successive deposition of the different layers of components of the sensitive layer On a polyimide substrate layer pretreated for 15 minutes with UV light in the presence of ozone, a first layer is screen printed with carbon ink to deposit the working electrode and 2 electrical tracks, the working electrode being contiguous to one of the electrical tracks. The strip is then dried in the oven at 120° C. for 10 minutes.

A second layer is then screen-printed with silver ink to deposit the reference electrode (also acting as a counter electrode), which is contiguous to the second electrical track. The strip is then dried in the oven at 120° C. for 10 minutes.

A third layer is then screen-printed with an insulating ink to partially cover the electrical tracks and the electrodes, leaving a part of the electrical tracks free so that the strip can be connected to the reader and a part of each electrode so that the uncovered part of the working electrode has an area of 1.25 mm$^2$ and the uncovered part of the reference electrode has an area of 1 mm$^2$. The strip is then dried in the oven at 120° C. for 10 minutes.

The following deposits are only applied to the uncovered part of the working electrode.

First, 1 µL of 0.2 g/L Prussian blue in an ethanol/water mixture (30/70 by volume) is deposited on the electrode and then the strip is oven-dried at 100° C. for 5 minutes.

An electrochemical test consisting of applying a potential difference of −0.2V between the working electrode and the second electrode for 30 s with a drop of phosphate buffer solution is then carried out and reduces the Prussian blue to Prussian white while controlling the quality of the strip via the current value measured after 30 seconds (threshold value −200 nA).

Then 1 µL of a mixture of 9 mM ATP (adenosine triphosphate) and 9 mM MgCl$_2$ (magnesium chloride) is deposited on the electrode (i.e., 9 nmol of each compound) and the electrode is dried for 5 minutes at 40° C. in a forced convection incubator.

Then 1 µL of a mixture of Glycerol Kinase (GK) at 1.5 U/µL and Glycerol-Phosphate Oxidase (GPO) at 0.5 U/µL is deposited on the electrode (i.e., 1.5 U of GK+0.5 U of GPO) and the electrode is dried for 3 minutes and 30 seconds at 40° C. in a forced convection incubator.

Then 1 µL of a mixture of 0.5% chitosan and 0.0025% glutaraldehyde in 0.5% acetic acid is deposited on the electrode and the electrode is dried for 4 minutes at 40° C. in a forced convection incubator.

The Prussian blue, co-factors (ATP+MgCl$_2$), enzymes (GK+GPO), membrane layer (chitosan) and crosslinker (glutaraldehyde) make up the sensitive layer.

A layer of double-sided adhesive is applied by pressure on the whole of the previously screen-printed insulating layer (covering it completely). This layer is 0.25 mm thick. The space left uncovered by this layer at the electrodes constitutes the measuring chamber (which therefore contains the 2 electrodes not covered by the insulating film).

A layer of polyethylene terephthalate (PET) protective film is then pressed onto the strip and acts as the top layer. It completely covers the double-sided adhesive layer as well as the space formed by the measuring chamber (without being in contact with the electrodes).

The strip thus manufactured is then stored in the dark at 4° C.

b. Strip produced by single layer deposition of the different components of the sensitive layer.

On a polyimide substrate layer pretreated for 15 minutes with UV light in the presence of ozone, a first layer is screen printed with carbon ink to deposit the working electrode and 2 electrical tracks, the working electrode being contiguous to one of the electrical tracks. The strip is then dried in the oven at 120° C. for 10 minutes.

A second layer is then screen-printed with silver ink to deposit the reference electrode (also acting as a counter electrode), which is contiguous to the second electrical track. The strip is then dried in the oven at 120° C. for 10 minutes.

A third layer is then screen-printed with an insulating ink to partially cover the electrical tracks and the electrodes, leaving a part of the electrical tracks free so that the strip can be connected to the reader and a part of each electrode so that the uncovered part of the working electrode has an area of 1.25 mm2 and the uncovered part of the reference electrode has an area of 1 mm2. The strip is then dried in the oven at 120° C. for 10 minutes.

The following deposit is only applied to the uncovered part of the working electrode. 1.5 μL of an aqueous solution containing 1.5 mM ferrocene methanol, 1 U/μL glycerol kinase, 0.33 U/μL glycerol phosphate oxidase, 1 U/μL peroxidase, 27 mM ATP, 27 mM $MgCl_2$, 0.25% hydroxypropyl methyl cellulose, 0.1% Triton X-100 and 1×PBS is deposited on the electrode and then the strip is oven dried at 40° C. for 5 minutes.

A layer of double-sided adhesive is applied by pressure on the whole of the previously screen-printed insulating layer (covering it completely). This layer is 0.25 mm thick. The space left uncovered by this layer at the electrodes constitutes the measuring chamber (which therefore contains the 2 electrodes not covered by the insulating film).

A layer of polyethylene terephthalate (PET) protective film is then pressed onto the strip and acts as the top layer. It completely covers the double-sided adhesive layer as well as the space formed by the measuring chamber (without being in contact with the electrodes).

The strip thus manufactured is then stored in the dark at 4° C.

Example 2: Measurement of the Quantity of Glycerol by Amperometry

Figure 5:
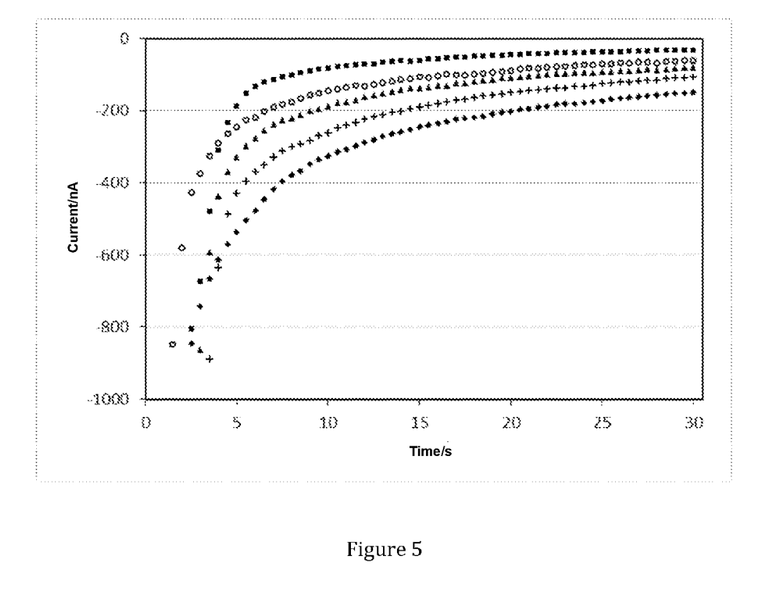
FIG. 5 is a graphical representation of the results of amperometric measurements taken on blood samples with glycerol added at different concentrations (square: 0 µM; round: 150 µM; triangle: 300 µM; cross: 500 µM; diamond: 700 µM, i.e., reading from top to bottom).
Figure 6:
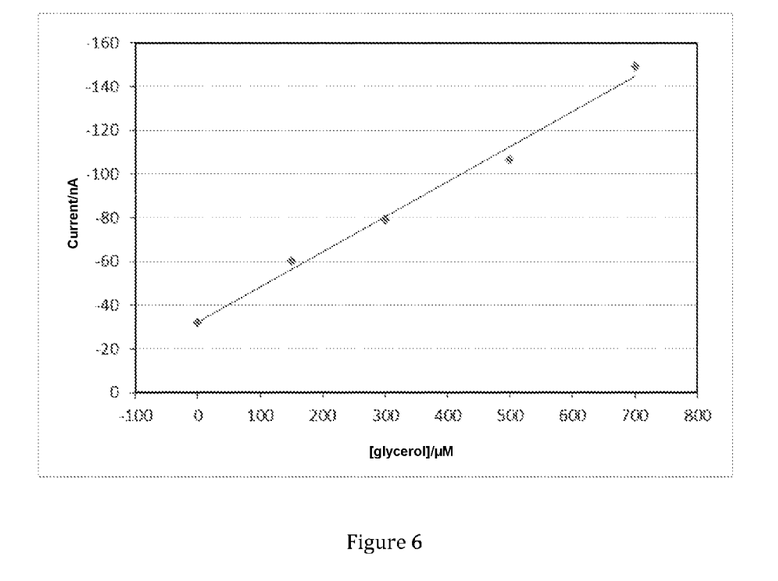
FIG. 6 is a graphical representation of the current obtained from the measurements shown in FIG. 5 as a function of the concentration of glycerol added to the samples. The calibration line obtained by linear regression is also shown.
Figure 7:
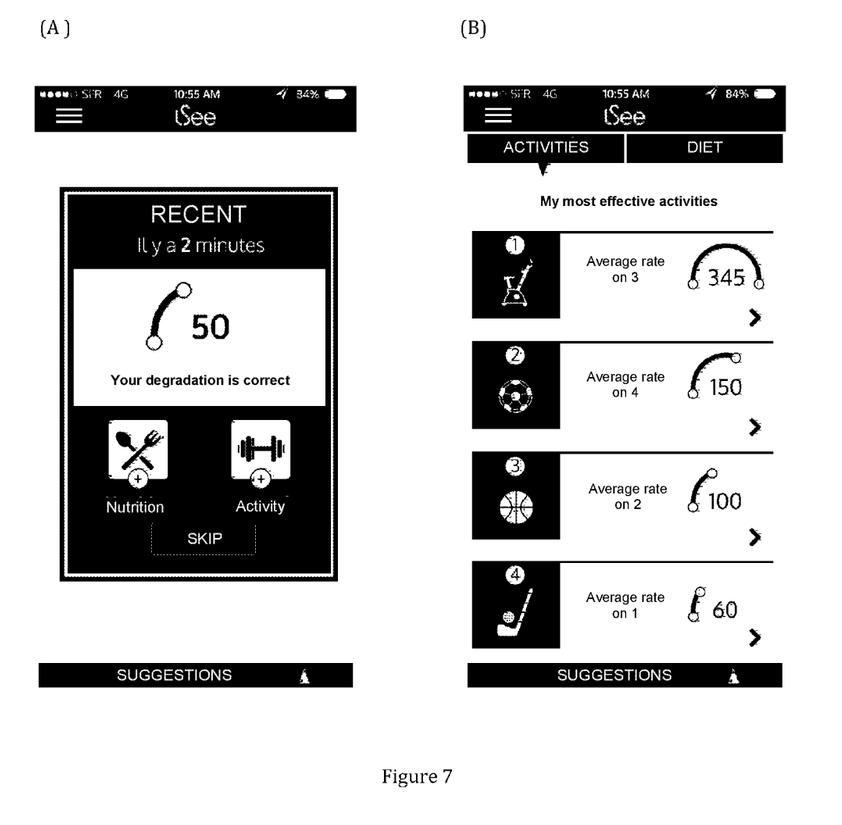
FIG. 7 shows two examples of visuals of the results that can be displayed to the user. In the display of FIG. 7 (A), the result of the immediately performed measurement is shown together with a comment correlated to this result. On the display in FIG. 7 (B), a ranking of the different types of physical activities according to the results of the measurement and/or previous measurements made by the user is displayed.

A drop of blood of approximately 3 μL is applied to the strip at the notch in the top layer.
  a. Protocol for detecting the amount of glycerol present in the blood sample
  This protocol is suitable for the use if a strip as described in Example 1a
  The sample is incubated in the measuring chamber for 3 seconds.
  Then an electrical potential difference of −0.2V is applied between the working electrode and the reference electrode.
  The current value is measured 30 seconds after the start of the potential difference application.
  b. Use of data to quantify lipolysis
  i. Construction of a calibration line using measurements at several concentrations
  As shown in FIG. 5, glycerol of known concentration was added to venous blood samples taken from a volunteer in order to obtain blood samples with different concentrations of added glycerol. These samples are analyzed using the technique described above and the current 30 seconds after application of the potential is noted and then related to the glycerol concentration of the sample to construct a calibration line.
    ii. Extraction of the directing coefficient of the line to link current and concentration.
  The calibration line as shown in FIG. 6 is then obtained by linear regression of the previously recorded data and the directing coefficient and ordinate pair at the origin of this calibration line is determined. These two parameters are pre-recorded in the application that interprets the measurements made by the user and allow the current values measured during tests to measure the degradation of fat mass to be interpreted in terms of the concentration of glycerol produced by lipolysis.

Example 3: Use of Data by a User

The user turns on the meter and inserts a test strip. It then generates a drop of capillary blood at the tip of a finger using a lancet device and deposits it in the notch of the test strip provided for this purpose.

The meter performs the amperometric measurement as described above and transmits the result to a second connected device, which may be the user's smartphone. The instrument uses the preset calibration data and translates the current value into the amount of degraded fat mass. This quantity is then displayed to the user via a screen on the second device. This quantity can also be analyzed by the device, such as a comparison with the user's previous measurements or an interpretation of the measurement in relation to external factors that the user has entered into the application, i.e., the type of physical exercise or the nutrients ingested.

The invention claimed is:

1. An electrochemical test strip for detecting glycerol in a body fluid sample, comprising:
  an electrically insulating substrate layer;
  at least two electrodes, at least a first electrode of the at least two electrodes comprising a working electrode comprising carbon and being functionalized with ferrocene derivatives in a reduced form, and at least a second electrode of the at least two electrodes comprising a reference electrode and a counter electrode;
  at least as many electrical tracks as the number of the at least two electrodes;
  an enzyme layer disposed on the at least two electrodes, the enzyme layer comprising glycerol-specific enzymes, the glycerol-specific enzymes selected from among the group consisting of:
    glycerol kinase and glycerol phosphate oxidase;
  a layer of co-factors selected from among the group consisting of:
    adenosine triphosphate and $MgCl_2$; and
  at least one membrane layer;
  a top layer; and
  a spacer layer located between the at least two electrodes and the top layer, the spacer layer creating a space defining a measuring chamber for receiving the sample, the measuring chamber at least partially covering the electrodes and the enzyme layer.

2. The strip of claim 1, wherein the at least a second electrode of the at least two electrodes comprises a single electrode configured to function as both the reference electrode and the counter electrode.

3. The strip of claim 1, wherein the at least a second electrode of the at least two electrodes comprises one electrode configured to function as the reference electrode and another electrode configured to function as the counter electrode.

4. The strip of claim 1, wherein the working electrode is functionalized with a ferrocene-methanol solution.

5. The strip of claim 1, further comprising a peroxidase.

6. The strip of claim 1, wherein the membrane comprises hydroxypropyl methyl cellulose.

7. The strip of claim 1, further comprising a surfactant and/or a cross-linking agent.

8. The strip of claim 1, wherein the enzymes, co-factors and membrane are contained in a single layer.

9. A method of forming an electrochemical strip, comprising:
  providing an electrically insulating substrate layer;
  forming at least two electrodes, at least a first electrode of the at least two electrodes comprising a working electrode comprising carbon and being functionalized with ferrocene derivatives in a reduced form, and at least a second electrode of the at least two electrodes comprising a reference electrode and a counter electrode;
  forming at least as many electrical tracks as the number of the at least two electrodes;
  forming an enzyme layer disposed on the at least two electrodes and containing glycerol-specific enzymes consisting of:
    glycerol kinase and glycerol phosphate oxidase; and
  forming a layer of co-factors consisting of:
    adenosine triphosphate and $MgCl_2$; and
  forming at least one membrane layer;
  forming a spacer layer; and
  forming a top layer, the spacer layer disposed between the at least two electrodes and the top layer.

10. The method of claim 9, further comprising adding a peroxidase to the strip.

11. The method of claim 9, further comprising forming the at least one membrane layer to comprise hydroxypropyl methyl cellulose.

12. The method of claim 9, further comprising forming the enzyme layer, the layer of co-factors and the at least one membrane layer to comprise a single layer.

* * * * *